United States Patent [19]

Yamaguchi et al.

[11] Patent Number: 4,482,742
[45] Date of Patent: Nov. 13, 1984

[54] PROCESS FOR PREPARING OF 3,3'-DIAMINO DIPHENYLSULFONES

[75] Inventors: Keizaburo Yamaguchi; Kenichi Sugimoto; Yoshimitsu Tanabe, all of Tokyo, Japan

[73] Assignee: Mitsui Toatsu Chemicals Inc., Tokyo, Japan

[21] Appl. No.: 466,498

[22] Filed: Apr. 12, 1983

[30] Foreign Application Priority Data

| | | | |
|---|---|---|---|
| Feb. 18, 1982 | [JP] | Japan | 57-23516 |
| Feb. 26, 1982 | [JP] | Japan | 57-28967 |
| May 21, 1982 | [JP] | Japan | 57-84890 |
| Dec. 23, 1982 | [JP] | Japan | 57-224977 |

[51] Int. Cl.³ .................. C07C 85/00; C07C 85/11; C07C 85/24
[52] U.S. Cl. .................. 564/412; 564/422; 564/423
[58] Field of Search .................. 564/412, 422, 423

[56] References Cited

U.S. PATENT DOCUMENTS

| | | | |
|---|---|---|---|
| 2,458,214 | 1/1949 | Souders | 564/422 |
| 2,823,235 | 2/1958 | Graham et al. | 564/423 |
| 3,472,897 | 10/1969 | Pryor et al. | 564/423 |
| 3,637,820 | 1/1972 | Dodman et al. | 564/422 X |
| 4,206,147 | 6/1980 | Daumas et al. | 564/412 |
| 4,206,148 | 6/1980 | Biola et al. | 564/412 |
| 4,207,261 | 6/1980 | Csikos | 564/422 X |

Primary Examiner—Paul F. Shaver
Attorney, Agent, or Firm—Kane, Dalsimer, Kane, Sullivan and Kurucz

[57] ABSTRACT

3,3'-diamino diphenylsulfones are prepared by catalytically reducing and dehalogenating, in the presence of a reduction catalyst and a dehydrohalogenation agent, a diphenylsulfone compound of the general formula

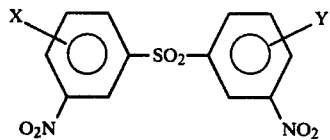

in which X is a halogen atom and Y is hydrogen or a halogen atom.

6 Claims, No Drawings

PROCESS FOR PREPARING OF 3,3'-DIAMINO DIPHENYLSULFONES

BACKGROUND OF THE INVENTION

The present invention relates to a novel process for preparing 3,3'-diamino diphenylsulfones.

3,3'-diamino diphenylsulfones are useful as monomers for heat-resistant polymers, agricultural or medical chemicals, intermediates for dyestuffs and the like. Particularly, they are important as raw materials for heat-resistant polyamide or polyimide resins.

In a conventional process, 3,3'-diamino diphenylsulfone is prepared by reduction of 3,3'-dinitrodiphenylsulfone [N. P. Ghatge et al, Angew, Makromol. Chem., 49 (1), 133 (1976); Japanese Patent Kokai Kōhō No. 56-25150; N. R. Ayyangar et al, Synthesis Communications, 640 (1981), Koristek et al, Czech. No. 158,469; Chem. Abstr., 84 16955 K (1976)]. In this process the starting 3,3'-dinitrodiphenylsulfone is prepared by nitration of diphenylsulfone with a mixed acid [C. A. Buehler et al, J. Org. Chem., 4 262 (1939); J. Lacroix, Bull. Soc. Chim., 35 1436-50 (1924); Chem. Abstr. 19 980] or by nitration and simultaneously oxidation of diphenylsulfide with fuming nitric acid [Baldo Ciocca et al, Gazz Chim. Ital., 76 113-19 (1946); Chem. Abstr., 40 7153 (1946)].

Also, there are known other processes in which 3,3'-dinitrodiphenylsulfone is isolated as by-products in the nitration of benzene in the presence of sulfuric anhydride [W. Alama et al, Biul. Wozskowez Akad. Tech., 13 57-63 (1964); Chem. Abstr., 73 34962 n (1970)] or as by-products in the preparation of m-nitrobenzenesulfonic acid by sulfonation of nitrobenzene [Nazvanova et al, Tr. Khim, Kkim. Tekknol., 178-9 (1969); Chem. Abstr., 73 34962 n (1970)].

However, in the process for the preparation of 3,3'-dinitrodiphenylsulfone starting from diphenylsulfone or diphenylsulfide, since the reaction products obtained by the nitration are a mixture containing isomers, it is necessary for the isolation of 3,3'-dinitrodiphenylsulfone to use a large amount of a solvent and to repeat a recrystallization refining. Therefore, the yield is greatly reduced and complicated operations for recovering the solvent used, for treating residuals and for treating a large amount of waste acids are required.

On the other hand, in the process of by-producing 3,3'-dinitrodiphenylsulfone in the nitration of benzene in the presence of sulfuric anhydride or in the sulfonation of nitrobenzene, there are disadvantages that the yield of end product is low and a necessary amount of supply can not be ensured because the main purpose of that process is not to produce 3,3'-dinitrodiphenylsulfone.

Also, it is known that 3,3'-dinitro-4,4'-dichlorodiphenylsulfone which is one of diphenylsulfone compounds used as the starting material in the present invention is prepared by nitration of 4,4'-dichlorodiphenylsulfone, for example, with an excess of a mixed acid (Ber 40, 640 (1907); Japanese Patent Kokai Kōhō No. 52-14744).

However, in this process the amount of the mixed acid used is large so that after treatment of waste acids becomes troublesome. Further, it is not easy to isolate the desired compound in a high purity from the reaction product, since the compound tends to take granular forms so as to bear the raw material and the acids therein. It is not easy to refine such compound after the completion of the reaction. It may be proposed to obtain the desired compound in a high purity by isolating said compound by means of filtering immediately after the crystallization from the mixed acid. However, such procedure is troublesome and impractical for commercial production of the desired compound. The process has a further disadvantage from the standpoint of operational easiness and economy in that, as the nitration reaction is exothermal, the reaction must be carried out by adding the raw material stepwise in small doses to the reactor and/or cooling the reactor efficiently.

It has been therefore highly desired to develop a process for commercially producing 3,3'-dinitro-4,4'-dichloro diphenylsulfone by the nitration of 4,4'-dichloro diphenylsulfone in which the reaction heat can be controlled in an easy manner, there is used minimal amount of the mixed acid, the treatments after the reaction can be easily made, and further there can be obtained crystalline 3,3'-dinitro-4,4'-dichloro diphenylsulfone in a high yield and purity.

SUMMARY OF THE INVENTION

It is an object of the present invention to provide a process for preparing 3,3'-diamino diphenylsulfone, which process is advantageous from the commercial standpoint, can produce the desired product in a high yield, and offers an easy treatment of waste liquids after the reaction.

It is another object of the present invention to provide a novel process for preparing 3,3'-dinitro-4,4'-dichloro diphenylsulfone, as starting material for the above mentioned process, in a high yield and purity.

It is a further object to provide a process for preparing 3,3'-diamino diphenylsulfone in which the reaction intermediates can be applied to the subsequent reaction steps, without need of separation of various isomers therefrom.

According to the present invention, there is provided a process for preparing 3,3'-diamino diphenylsulfone which comprises catalytically reducing and dehalogenating, in the presence of a reduction catalyst and a dehydrohalogenation agent, a diphenylsulfone compound of the general formula

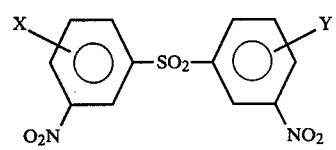

in which X is a halogen atom and Y is hydrogen or a halogen atom.

According to the present invention, there is also provided a process for preparing crystalline 3,3'-dinitro-4,4'-dichloro diphenylsulfone in a high yield and purity which comprises nitrating 4,4'-dichloro diphenylsulfone in a fatty halogenated hydrocarbon solvent.

According to the present invention, there is further provided a process for preparing 3,3'-diamino diphenylsulfone in a high yield which comprises reacting 4-chlorobenzenesulfonic acid or 4-chlorobenzenesulfonyl chloride with chlorobenzene to produce a mixture of dichloro diphenylsulfone, nitrating directly said mixture (i.e. without said mixture having been subject to any refining operation) to produce a mixture of dinitro dichloro diphenylsulfone, and then catalytically reducing and dechlorinating said mixture in the presence of a reduction catalyst and dehydrochlorination agent.

DETAILED DESCRIPTION OF THE INVENTION

The process of the present invention can produce 3,3'-diamino diphenylsulfone in a high yield at a lower cost, without causing the environmental pollution due to wastes. Furthermore, the desired compound can be isolated at a high purity from the reaction product, without need for complicated refining operations. Thus, the process of the present invention is very suitable for commercially producing 3,3'-diamino diphenylsulfone.

The nitration in the process of the present invention, where there is used a fatty halogenated hydrocarbon solvent, is advantageous in that the control of the reaction heat is carried out in an easy manner, the amount of the mixed acid used is smaller, and it is easy to recover the solvent for reuse if required. Thus, the process is effective for producing 3,3'-dinitro-4,4'-dichloro diphenylsulfone in a high yield and purity.

According to the process of the present invention, it is also possible to produce 3,3'-diamino diphenylsulfone from 4-chlorobenzenesulfonic acid or 4-chlorobenzenesulfonyl chloride as starting material, where the products in the forms of mixtures containing various isomers produced in the intermediate steps can be directly applied to the subsequent steps without need of refining such products to separate the desired product therefrom.

In general, it is well-known that dichlorodiphenyl sulfones are produced by a dehydration condensation reaction between chlorobenzenesulfonic acid and chlorobenzene, for example, in the presence of a super strong acid resin (perfluorosulfonic acid type resin; Nafion-H, the trade name by Du Pont) (Japanese Patent Kokai Koho No. 57-85363), or by a dehydrochlorination condensation reaction between chlorobenzenesulfonyl chloride and chlorobenzene, the former, for example, being produced by reaction of 4-chlorobenzenesulfonic acid and thionyl chloride or phosphorus oxychloride (Japanese Patent Publication No. 56-5386; U.S. Pat. No. 3,125,604).

In these processes, the main product is 4,4'-dichlorodiphenylsulfone and the remainder is 2,4'-dichlorodiphenylsulfone and 3,4'-dichlorodiphenylsulfone. The composition ratio of the 4,4'-form:2,4'-form:3,4'-form is approximately 89-93:3-7:0.5-3. The 4,4'-form of end product is obtained with a yield of 65-80% by recrystallization. On the other hand, it is known that dinitrodichlorodiphenylsulfone is produced with high yield by nitration of dichlorodiphenylsulfone with a mixed acid [Ber., 40 640 (1907); Japanese Patent Kokai Koho No. 52-14744].

As mentioned above, the reaction product of 4-chlorobenzenesulfonic acid or 4-chlorobenzenesulfonyl chloride with chlorobenzene is in the form of a mixture of various isomers. It is therefore necessary to isolate the desired compound from such a mixture if it is intended to use as starting material for a specific product. However, if the nitration is conducted on a mixture mainly consisting of 4,4'-dichloro diphenylsulfone, and 2,4'-dichloro diphenylsulfone, all the dichloro diphenylsulfones are nitrated at their m- and m'-positions with respect to the sulfonyl group to produce 3,3'-dinitro-4,4'-dichloro diphenylsulfone and 5,3'-dinitro-2,4'-dichloro diphenylsulfone and all these dinitro-dichloro diphenylsulfones will convert, through the reduction and dechlorination according to the present invention, to 3,3'-diamino diphenylsulfone.

On the other hand, 3,4'-dichlorodiphenylsulfone of the minor component is considered to be converted to 5,3'-dinitro-3,4'-dichlorodiphenylsulfone and 4,3'-dinitro-3,4'-dichlorodiphenylsulfone. The former is converted to 3,3'-diaminodiphenylsulfone by the reduction and dechlorination according to the present invention, while 3,4'-diaminodiphenylsulfone derived from the latter is easily removed, for example, by recrystallization.

Thus, according to the process of the present invention in which there is produced 3,3'-diamino diphenylsulfone through the three steps of the condensation reaction, the nitration reaction and the reduction-dechlorination reaction and the intermediates can be used in the production of 3,3'-diamino diphenylsulfone without refining operations of such intermediates. The present invention therefore offers commercially acceptable low-cost process for the production of 3,3'-diamino diphenylsulfone, because of easy operation and high yield and purity of the desired product.

The compound of the formula I as defined above can be expressed specifically in the following manners:

A diphenylsulfone compound of the general formula

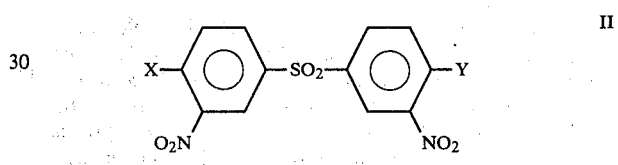

II in which X and Y are the same or different halogen atoms;

A diphenylsulfone compound of the general formula

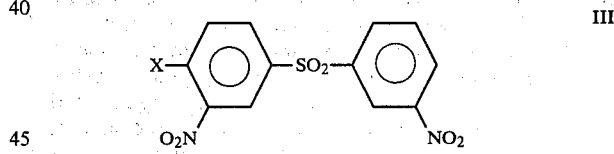

III in which X is a halogen atom;

A diphenylsulfone compound of the general formula

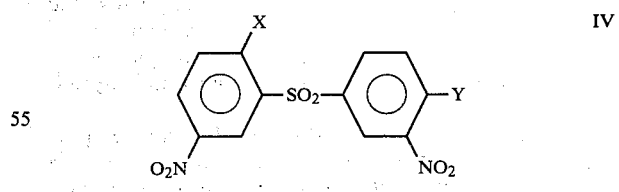

IV in which X and Y are the same or different halogen atom.

Examples of the compound of Formula II include 3,3'-dinitro-4,4'-dichlorodiphenylsulfone, 3,3'-dinitro-4,4'-dibromodiphenylsulfone, 3,3'-dinitro-4,4'-difluorodiphenylsulfone, 3,3'-dinitro-4,4'-diiododiphenylsulfone, 3,3'-dinitro-4-chloro-4'-bromodiphenylsulfone and 3,3'-dinitro-4-chloro-4'-iododiphenylsulfone.

Examples of the compound of Formula III include 3,3'-dinitro-4-chlorodiphenylsulfone, 3,3'-dinitro-4- bromodiphenylsulfone, 3,3'-dinitro-4-fluorodiphenylsulfone and 3,3'-dinitro-4-iododiphenylsulfone.

Examples of the compounds of Formula IV include 2,4'-dichloro-5,3'-dinitrodiphenylsulfone, 2,4'-dibromo-5,3'-dinitrodiphenylsulfone, 2,4'-difluoro-5,3'-dinitrodiphenylsulfone, 2-chloro-4'-bromo-5,3'-dinitrodiphenylsulfone, 2-chloro-4'-fluoro-5,3'-dinitrodiphenylsulfone, 2-chloro-4'-iodo-5,3'-dinitrodiphenylsulfone, 2-bromo-4'-chloro-5,3'-dinitrodiphenylsulfone, 2-bromo-4'-fluoro-5,3'-dinitrodiphenylsulfone, 2-fluoro-4'-chloro-5,3'-dinitrodiphenylsulfone, 2-fluoro-4'-bromo-5,3'-dinitrodiphenylsulfone and 2-iodo-4'-chloro-5,3'-dinitrodiphenylsulfone.

It is advantageous from the commercial standpoint to utilize the diphenylsulfones having chlorine atoms as halogens.

The halogeno dinitro diphenylsulfones as exemplified above can be easily prepared by the nitration of the corresponding halogeno diphenylsulfones such as 4,4'-dihalogeno diphenylsulfone, 4-halogeno diphenylsulfone, or 2,4'-dihalogeno diphenylsulfone. For example, 3,3'-dinitro-4,4'-dichlorodiphenylsulfone is obtained with a yield of 90–97% of the nitration of 4,4'-dichlorodiphenylsulfone with a mixed acid [Japanese Patent Kokai Koho No. 52-14744; W. F. Hart et al, J. Org. Chem., 27 338 (1962)]. 3,3'-Dinitro-4-chlorodiphenylsulfone is obtained with high yield by the nitration of 4-chlorodiphenylsulfone with a mixed acid [A. V. Lvanov et al, J. Org. Chem. of USSR, 14 557–559 (1978)].

However, according to an alternative method as mentioned below, 3,3'-dinitro-4,4'-dichlorodiphenylsulfone is conveniently produced by the nitration of 4,4'-dichlorodiphenylsulfone in an aliphatic halogenated hydrocarbon solvent. The solvents which may be used in this method are, for example, dichloro methane, chloroform, carbon tetrachloride, 1,1-dichloro ethane, 1,2-dichloro ethane, 1,1,1-trichloro ethane, 1,1,2-trichloro ethane, 1,1,1,2-tetrachloro ethane, 1,1,2,2-tetrachloro ethane, 1,2-dichloro ethylene, trichloro ethylene and tetrachloro ethylene. While there is no limitation on the amount of the solvent, it is general that the solvent is used 0.2–20 times by weight, preferably 1–10 times by weight, based on 4,4'-dichloro diphenylsulfone. In this method there is employed the mixed acid or a nitrate + sulfuric acid as nitrating agent. Nitric acid is used in an amount of 2.0–5.0 times, more preferably 2.2–3.0 times, by mols based on the amount of 4,4'-dichloro diphenylsulfone. While concentration of nitric acid is not critical, it is general to use nitric acid of a specific gravity of 1.30–1.52, more preferably 1.42–1.50. It is preferred to use a nitrate in an amount of 2–3 times in mols, more preferably 2.1–2.5 times in mols, based on the raw material. As preferred nitrates, there can be exemplified sodium nitrate and potassium nitrate. Sulfuric acid used preferably in an amount of 2–8 times in mols, more preferably 4–6 times in mols based on the raw material. Concentration of sulfuric acid had best be more than 70%.

This method may be carried out by adding the mixed acid dropwise to 4,4'-dichloro diphenylsulfone dissolved in the organic solvent, or by adding the organic solvent to 4,4'-dichloro diphenylsulfone in the mixed acid. Otherwise, the method may be conducted by adding 4,4'-dichloro diphenylsulfone to a mixture of the mixed acid and the organic solvent. In case where a nitrate is employed in place of nitric acid, it is general that to 4,4'-dichloro diphenylsulfone in the organic solvent there is added nitric acid and then sulfuric acid dropwise. The reaction temperature is in the range of 20°–100° C., preferably 40°–80° C. The reaction is generally completed in 2–10 hours.

After the completion of the reaction, the organic phase is separated from the mixed acid phase. Then, the solvent is distilled out from the organic phase which is then filtered, washed with water and dried to give a high yield and purity of 3,3'-dinitro-4,4'-dichloro diphenylsulfone crystals.

The diphenylsulfone compounds of the abovementioned general formula I to be used in the process of the present invention may be in the form of a mixture of various dinitro-dichloro diphenylsulfones produced by the nitration of a reaction mixture which has been produced by reaction of 4-chlorobenzenesulfonic acid or 4-chlorobenzenesulfonyl chloride with chlorobenzene.

In such a method, firstly the reaction of 4-chlorobenzenesulfonic acid or 4-chlorobenzenesulfonyl chloride and chlorobenzene is carried out, which is hereinafter referred to as the first step of the reaction. In the first step reaction, the amount of chlorobenzene is 1.1–3 times in mols based on the 4-chlorobenzenesulfonic acid.

A catalyst is normally used in the first step of the reaction, representative of such catalyst being super strong acid resins (e.g. Nafion-H, the tradename by Du Pont). The amount of catalyst used is 5–300% by weight based on the chlorobenzenesulfonic acid.

The first step of reaction is carried out at a temperature of 80°–200° C. while removing the resulting water. Thus, the completion of the reaction may be detected through the determination of the amount of water formed or through the determination of consumption of 4-chlorobenzenesulfonic acid by a suitable means such as gas chromatography or high performance liquid chromatography.

On the other hand, in case of the reaction of 4-chlorobenzenesulfonyl chloride with chlorobenzene, the latter is used in an amount of 1.1–3 times by mol based on the former.

Any type of catalyst generally used in Fridle-Crafts' reaction may be applied in this reaction, representative of such catalyst being anhydrous aluminum chloride, anhydrous ferric chloride, ferric sulfate, and boron trifluoride. Anhydrous ferric chloride is most often used because of low cost and easy handling. The amount of catalyst used is 0.5–10 molar %, preferably 1–5 molar % based on 4-chlorobenzenesulfonyl chloride.

The reaction proceeds at reflux by excessive chlorobenzene, i.e. at a temperature of 140°–180° C. until the production of hydrochloric acid ceases. Thus, the completion of the reaction may be detected through the determination of the product of hydrochloric acid gas or through the determination of consumption of 4-chlorobenzenesulfonyl chloride by a suitable means such as gas chromatography or high performance liquid chromatography.

After the completion of the reaction, unreacted chlorobenzene is removed out of the reaction system by means of vacuum distillation or steam distillation to obtain a mixture of dichlorodiphenylsulfones.

The mixture of dichlorodiphenylsulfones is then subjected to a nitration reaction to produce dinitrodichloro-diphenylsulfones, which reaction is referred to as the second step of the reaction. While any type of conventional nitrating agent may be used including the mixed acid, fuming nitric acid and nitric acid + acetic acid, it is general to use the mixed acid or fuming nitric acid. When the nitration is carried out using fuming nitric acid, 80–95% nitric acid is used in an amount of 8–12 times in mols based on the crude dichlorodiphenylsulfones. When the nitration is carried out using a combination of nitric acid or a nitrate (such as sodium nitrate or potassium nitrate) plus concentrated sulfuric acid, the molar proportion of the crude dichlorodiphenylsulfones:nitric acid or nitrate:concentrated sulfuric acid is in the range of 1:2.1–3.0:4–6. If required, use may be made, in the nitration, of a halogenated hydrocarbon solvent such as methylene chloride, 1,2-dichloro ethane, 1,1,2-trichloro ethane, chloroform, carbon tetrachloride, 1,1,2,2-tetrachloro ethane or trichloro ethane.

The nitration reaction may be carried out by mixing together the crude dichlorodiphenylsulfones, a nitrating agent and, if required, a solvent. However, the nitration may be carried out, particularly in the case where the mixed acid is employed as nitrating agent, by adding the crude dichlorodiphenylsulfones to the mixed acid or by adding nitric acid (or a nitrate) to a mixture of the crude dichlorodiphenylsulfones and sulfuric acid. By heating the crude dichlorodiphenylsulfones and the mixed acid while stirring, the nitration reaction proceeds. Preferably, reaction temperature is in the range of 50°–100° C. and reaction time is in the range of 2–10 hours. The completion of the reaction can be detected by thin layer chromatography or high performance liquid chromatography.

After the completion of the reaction, the desired compounds are separated from the product in any conventional manner: For example, when solvent was not used, the product is diluted with water and then subjected to a filtering. Otherwise, when solvent was used, the solvent phase is separated from the acid phase, and then the solvent is distilled out by steam distillation. The precipitate is filtered to give, as product of the second step of the reaction, a mixture of various types dinitro-dichloro diphenylsulfones such as 3,3'-dinitro-4,4'-dichloro diphenylsulfone and 5,3'-dinitro-2,4'-dichloro diphenylsulfone.

Such mixture of various dinitro-dichloro diphenylsulfone can be applied, without need of isolating dinitro-dichloro diphenylsulfones from each other, to the subsequent reduction-dechlorination reaction (the third step of reaction) to yield the end 3,3'-diamino diphenylsulfone.

The third step of reaction may be carried out in the following manner: (A) To the crude diphenylsulfone dissolved or suspended in a solvent there is added a reduction catalyst. Then, the mixture is introduced with hydrogen at a predetermined temperature, while stirring. Dechlorination reaction follows by the addition of a dehydrochlorination agent. Otherwise, (B) a dehydrochlorination agent is added at the time of addition of a reduction catalyst, and then there is introduced hydrogen into the mixture at a predetermined temperature while being stirred, so that reduction reaction of the nitro groups and dechlorination will proceed simultaneously. In both cases, the reaction proceeds smoothly to produce the desired compound, 3,3'-diamino diphenylsulfone. However, because of nucleophilic nature of the halogen atoms of the starting diphenylsulfone compounds, in the method (B) there may occur some side reactions with dehydrochlorination agent so as to decrease the yield of the desired compound. The method (A) is therefore preferred.

There can be used many metal catalysts which have been generally used in a catalytic reduction. For example, nickel, palladium, rhodium, ruthenium, cobalt or copper may be used as the reduction catalyst in the process of the present invention. From commercial standpoint, it is preferable to use a palladium catalyst. While these catalysts may be used in metallic states, it is general that they are supported on carriers such as carbon, barium sulfate, silica gel or alumina. Such metal as nickel, cobalt or copper may be used in the form of a Raney catalyst. The amount of reduction catalyst to be used is in the range of 0.01–10% by weight as metal (generally, 2–8% by weight when used in metallic state, while 0.1–5% by weight when used in the form of supported catalyst) on the basis of the amount of the diphenylsulfone of the formula I as raw material.

As dehydrohalogenation agents to be used in the process of the present invention, there can be exemplified oxides, hydroxides, carbonates or bicarbonates of alkaline or alkaline earth metals, ammonia and organic amines. More specifically, such compounds as calcium carbonate, sodium hydroxide, magnesium oxide, ammonium bicarbonate, calcium oxide, lithium hydroxide, barium hydroxide, potassium carbonate, potassium hydroxide, ammonia, triethyl amine, tri-n-butyl amine, triethanol amine, pyridine or N-methyl morpholine. A mixture of two or more of such dehydrohalogenation agents may be used. The amount of dehydrohalogenation agent is generally in the range of 0.5 to 5 times, preferably 1 to 3 times by mol, based on the diphenylsulfone.

The reduction and dehalogenation reaction is generally carried out using a solvent. There is no limitation on the type of solvent to be used unless it is extremely inactive. Thus, there can be used such solvents as alcohols such as methanol, ethanol, or isopropyl alcohol, ethers such as dioxane, tetrahydrofuran or methylcellosolve, fatty hydrocarbons such as hexane or cyclohexane, aromatic hydrocarbon such as benzene, toluene, or xylene, esters such as ethyl acetate or butyl acetate, halogenated hydrocarbons such as dichloro methane, chloroform, carbon tetrachloride, 1,2-dichloro ethane, 1,1,2-trichloro ethane or tetrachloro ethane, N,N-dimethyl formamide or dimethyl sulphoxide. If the reaction rate is slow in the use of a solvent immiscible with water, there may be used a conventional interphase transfer catalyst such as a quarternary ammonium salt or phosphonium salt to accelerate the reaction. The amount of solvent is not limited as long as the starting diphenylsulfone is suspended or dissolved in the solvent. Generally, it is sufficient to use solvent in an amount of 0.5 to 10 times based on the raw material.

There is no limitation on reaction temperature, and the reaction is generally in the range of 20°–200° C., more preferably in the range of 20°–100° C. Reaction pressure is generally in the range of atmospheric pressure to 50 Kg/cm$^2$.G.

The degree of the reaction can be detected by determination of the calculated amount of hydrogen absorbed or by thin layer chromatography. After removal of the catalyst and the inorganic salts by such a procedure as heat filtering or extraction, from the reaction system, concentration procedure is carried out depending upon requirement to give crystals of 3,3'-diamino diphenylsulfone. Alternatively, there is introduced to the reaction liquid dry hydrochloric gas, out of which the catalyst and the inorganic salts have been separated, to obtain 3,3'-diamino diphenylsulfone in the form of hydrochloric acid addition salt.

The process of the present invention will be more illustrated by the following examples.

EXAMPLE 1

57.4 g (0.2 moles) of 4,4'-dichloro diphenylsulfone is dissolved in 170 ml of 1,2-dichloro ethane. Following addition of 28.2 g of nitric acid (specific gravity 1.50) at room temperature, to the resultant mixture there is added 98% sulfuric acid dropwise during 30 minutes at 30°–40° C. After stirring for 7 hours at 70°–80° C., the mixture is cooled and then separated into an organic layer and a mixed acid layer. The solvent is removed by steam distillation. The precipitate is filtered, washed with water and dried to give needle-like crystals of 3,3'-dinitro-4,4'-dichloro diphenylsulfone (74.6 g). Yield 99%. Purity determined by high performance liquid chromatography is 99.6%. Melting point 201°–202° C. By recrystallization from ethanol there is obtained needle-like pure crystals. M.P. 201°–202° C.

Elemental Analysis:

|  | C | H | N | S | Cl |
|---|---|---|---|---|---|
| Calc. (%) | 38.21 | 1.59 | 7.43 | 8.49 | 18.81 |
| Found (%) | 38.26 | 1.60 | 7.41 | 8.52 | 18.82 |

EXAMPLES 2 AND 3

The procedure of Example 1 was repeated except using reaction conditions as set forth in Table I.

TABLE I

| Run No. | Solvent ml | Nitric acid g (sp. gr.) | Sulfuric acid g | React. temp. °C. | React temp. hr | Yield % | Purity % |
|---|---|---|---|---|---|---|---|
| 1 | 1,2-Dichloroethane 170 | 28.2 (1.50) | 98 | 70–80 | 7 | 99 | 99.6 |
| 2 | Dichloromethane 230 | 28.2 (1.50) | 98 | 40–45 | 10 | 99 | 99.4 |
| 3 | Carbon tetrachloride 230 | 28.2 (1.50) | 90 | 70–80 | 4 | 99 | 99.6 |

EXAMPLE 4

To a closed glass vessel equipped with a thermometer and a stirrer, there are added 113 g (0.3 moles) of 3,3'-dinitro-4,4'-dichloro diphenylsulfone, 8.5 g of 5% palladium/active carbon catalyst (available from Nihon Engelhardt Co.) and 300 ml of dioxane. While the mixture is being stirred at 70°–80° C., hydrogen is introduced in the vessel so that 40 l (1.79 moles) of hydrogen is absorbed into the mixture over 10 hours. After addition of 80 g (0.6 moles) of 30% aqueous sodium hydroxide, hydrogen is again introduced to the vessel with the mixture being stirred at 70°–80° C., so that it is absorbed 14.5 l (0.65 moles) over 5 hours. The reaction solution is filtered at 70°–80° C. to remove the catalyst. On cooling the solution, there is obtained 3,3'-diamino diphenylsulfone, as light brown crystals. The crystals are filtered, washed with 30 ml of 50% aqueous solution of dioxane and dried. Yield 66 g (89%). M.P. 170°–172° C. By recrystallization from ethanol there is obtained slightly brown prism pure crystals. M.P. 172.5°–173° C.

Elemental Analysis:

|  | C | H | N | S |
|---|---|---|---|---|
| Calc. (%) | 58.0 | 4.9 | 11.3 | 12.9 |
| Found (%) | 58.3 | 4.8 | 11.3 | 12.5 |

EXAMPLE 5–12

The procedures as in Example 4 are repeated, by varying 3,3'-dinitro-4,4'-dihalogeno diphenylsulfone as starting materials, catalysts and amounts thereof, solvents and amounts thereof, dehydrohalogenation agents and amounts thereof, temperatures and pressures. The results are shown in Table II.

TABLE II

| Example No. | Feed Materials X—⟨O⟩—SO₂—⟨O⟩—Y, O₂N, NO₂ | | | Catalyst | (g) | Solvent | (ml) | Dehydro-halogenation agent | (mole) | Reaction Conditions | | | Yield (%) |
|---|---|---|---|---|---|---|---|---|---|---|---|---|---|
| | X | Y | (mole) | | | | | | | Temp. (°C.) | Pressure Kg/cm²·G | Time (hr) | |
| 4 | Cl | Cl | 0.3 | 5% Pd/C | 8.5 | Dioxane | 300 | 30% Aqueous NaOH Solution | 0.6 | 70–80 | Atm. Pre. | 15 | 89 |
| 5 | Cl | Cl | 0.3 | Raney Nickel | 8.5 | Dioxane | 300 | Triethanol amine | 0.6 | 90–100 | 5–7 | 20 | 92 |
| 6 | Cl | Cl | 0.2 | 5% Pd/C | 5.5 | Ethanol | 300 | 30% Ammonia Water | 0.6 | 60–70 | 2–3 | 10 | 85 |
| 7 | Br | Cl | 0.1 | 5% Pd/C | 2 | Dioxane | 100 | Ca(OH)₂ | 0.3 | 70–80 | Atm. Pre. | 10 | 87 |
| 8 | I | Cl | 0.1 | 5% Pd/C | 2 | Ethylene glycol | 100 | MgO | 0.3 | 100–110 | Atm. Pre. | 6 | 81 |
| 9 | Br | Br | 0.1 | 5% Pt/C | 4 | Dioxane | 100 | Triethyl amine | 0.2 | 70–80 | Atm. Pre. | 12 | 81 |
| 10 | F | F | 0.1 | 5% Pd/C | 2 | Ethanol | 100 | 30% Aqueous NaOH Solution | 0.2 | 30–40 | Atm. Pre. | 8 | 86 |
| 11 | Cl | Cl | 0.3 | Pd | 1 | DMF | 200 | 30% Aqueous | 0.6 | 90–100 | Atm. | 12 | 83 |

TABLE II-continued

| | Feed Materials | | | | | | | | Reaction Conditions | | | |
|---|---|---|---|---|---|---|---|---|---|---|---|---|
| | X—⟨O⟩—SO$_2$—⟨O⟩—Y | | | | | | | | | Pressure | | |
| Example No. | O$_2$N X | Y | (mole) | Catalyst | (g) | Solvent | (ml) | Dehydro-halogenation agent | (mole) | Temp. (°C.) | Kg/cm$^2$·G | Time (hr) | Yield (%) |
| 12 | Cl | Cl | 0.1 | powder 5% Pd/C | 5.5 | Ethyl acetate | 200 | KOH Solution Pyridine | 0.2 | 50–60 | Pre. Atm. Pre. | 11 | 91 |

EXAMPLE 13

There are added 38 g (0.1 moles) of 3,3'-dinitro-4,4'-dichloro diphenylsulfone, 1 g of palladium black catalyst and 200 ml of benzene. While the mixture being stirred at 65°–70° C., hydrogen is introduced and 13 l (0.58 moles) of hydrogen is absorbed therein during about 9 hours. Then, after there are added 40 g (0.3 moles) of 30% aqueous solution of sodium hydroxide and 2 g of 90% aqueous solution of trioctylmethyl ammonium chloride (available from Tokyo-Kasei Co.), additional hydrogen, 5 l (0.22 moles), is introduced during about 7 hours while the mixture being stirred at 65°–70° C. The mixture at that temperature is filtered to remove the catalyst. Organic phase is separated from the filtrate, added with magnesium sulfate for removing water and then blown with dry hydrochloric gas to saturation. The precipitate thus obtained is filtered, washed with 30 ml of benzene and dried to obtain 25.5 g (yield 80%) of 3,3'-diamino diphenylsulfone in the hydrochloric acid salt form. Recrystallization from 10% aqueous isopropyl alcohol gives pure compound, as white needle-like crystals. M.P. 262°–264° C.

Elemental Analysis:

| | C | H | N | S | Cl |
|---|---|---|---|---|---|
| Calc. (%) | 44.8 | 4.4 | 8.7 | 10.0 | 22.1 |
| Found (%) | 44.9 | 4.6 | 8.7 | 10.1 | 22.2 |

EXAMPLE 14

To an autoclave are charged 38 g (0.1 mol) of 3,3'-dinitro-4,4'-dichlorodiphenylsulfone, 6 g (0.15 mols) of magnesium oxide, 2 g of 5% palladium-alumina catalyst and 300 ml of 1,2-dichloroethane. Hydrogen is introduced under stirring at temperatures of 30°–35° C. and reaction is effected while maintaining the pressure at 10 Kg/cm$^2$.G for 10 hours. After completion of the reaction the temperature of the reaction mixture is elevated to 70° C. and heat-filtrating is effected to remove the catalyst. On cooling 3,3'-diaminodiphenylsulfone is deposited as light brown crystals. The crystals are filtered, washed with 10 ml of 1,2-dichloroethane and dried. 16 g (Yield: 64.5%). M.P. 171°–172° C.

EXAMPLE 15

103 g (0.3 mols) of 3,3'-dinitro-4-chlorodiphenylsulfone, 8.5 g of 5% palladium/active carbon catalyst (available from Nihon-Engelhardt Co.) and 300 ml of dioxane are charged to an autoclave. With the mixture being stirred at 70°–80° C., hydrogen is introduced into the vessel so that 40.3 l (1.8 moles) of hydrogen is absorbed in the mixture over about 10 hours. Then, after 53 g (0.4 moles) of 30% aqueous solution of caustic soda is added, hydrogen is further introduced at 70°–80° C. with the mixture being stirred so that an additional 7.3 l (0.33 moles) is absorbed during four hours. The reaction liquid is filtered at 70°–80° C. so as to remove the catalyst and then allowed to cool giving light brown crystals of 3,3'-diamino diphenylsulfone. The crystals is filtered, washed with 30 ml of 50% aqueous solution of dioxane, and dried. Yield 92% (68.5 g). M.P. 170.5°–172° C. Recrystallization from ethanol gives slightly brown prism pure crystals. M.P. 173° C.

Elemental Analysis:

| | C | H | N | S |
|---|---|---|---|---|
| Calc. (%) | 58.0 | 4.9 | 11.3 | 12.9 |
| Found (%) | 58.1 | 5.0 | 11.3 | 12.7 |

EXAMPLES 16–22

The same procedures as in Example 15 are repeated except that the types of 3,3'-dinitro-4-halogeno diphenylsulfone, the types of catalyst and amounts thereof, type of solvents and amounts thereof, reaction temperatures and pressures are changed as given in Table III in which the results of the respective reactions are also set forth.

TABLE III

| | Feed Materials | | | | | | | | Reaction Conditions | | | |
|---|---|---|---|---|---|---|---|---|---|---|---|---|
| | X—⟨O⟩—SO$_2$—⟨O⟩ | | | | | | | | | Pressure | | |
| Example No. | O$_2$N X | NO$_2$ (mole) | Catalyst | (g) | Solvent | (ml) | Dehydro-halogenation agent | (mole) | Temp. (°C.) | Kg/cm$^2$·G | Time (hr) | Yield (%) |
| 15 | Cl | 0.3 | 5% Pd/C | 8.5 | Dioxane | 300 | 30% Aqueous NaOH Solution | 0.4 | 70–80 | Atm. Pre. | 14 | 92 |
| 16 | Cl | 0.3 | Raney Nickel | 8 | Dioxane | 300 | Triethylamine | 0.3 | 80–90 | 3–5 | 20 | 91 |
| 17 | Cl | 0.3 | 5% Pt/C | 8.5 | Ethanol | 300 | 30% Ammonia Water | 0.3 | 60–70 | 2–3 | 16 | 83 |
| 18 | Cl | 0.3 | 5% Pd/C | 8.5 | DMF | 200 | 30% Aqueous KOH Solution | 0.4 | 70–80 | Atm. Pre. | 10 | 87 |
| 19 | Br | 0.1 | 5% Pd/C | 2 | Ethylene | 100 | Magnesium | 0.08 | 100–110 | Atm. | 4.5 | 85 |

TABLE III-continued

| | Feed Materials | | | | | | | Reaction Conditions | | | |
|---|---|---|---|---|---|---|---|---|---|---|---|
| Example No. | $O_2N$—⌬—$SO_2$—⌬—$NO_2$ X | (mole) | Catalyst | (g) | Solvent | (ml) | Dehydro- halogenation agent | (mole) | Temp. (°C.) | Pressure Kg/cm²·G | Time (hr) | Yield (%) |
| 20 | F | 0.1 | 5% Pd/C | 2 | glycol Dioxane | 100 | oxide Triethanol amine | 0.1 | 70–80 | Pre. Atm. | ', 9 | 91 |
| 21 | I | 0.1 | 5% Pd/C | 2 | Ethyl acetate | 100 | 30% Aqueous $NaCO_3$ Solution | 0.12 | 30–40 | Pre. Atm. | 9 | 88 |
| 22 | Cl | 0.3 | Pd powder | | Methyl cellosolve | 300 | Pyridine | 0.3 | 90–100 | Atm. Pre. | 9 | 89 |

EXAMPLE 23

To a vessel are added 34.3 g (0.1 moles) of 3,3'-dinitro-4-chloro diphenylsulfone, 1 g of palladium black catalyst and 200 ml of benzene. While the mixture being stirred at 65°–70° C., hydrogen is introduced so that 13.7 1 (0.61 moles) of hydrogen is absorbed into the mixture during about 9 hours. 20 g (0.15 moles) of 30% aqueous solution of sodium hydroxide and 2 g of 90% aqueous solution of trioctyl methyl ammonium chloride (from Tokyo-Kasei Co., Japan) are added and then an additional amount of hydrogen, 2.4 1 (0.11 moles), is introduced during about 3 hours while the mixture being stirred at 65°–70° C. The reaction solution is filtered at that temperature to remove the catalyst and the organic phase is separated. After there is added magnesium sulfate to the organic phase for water-removal, dry hydrochloric gas is blown into the phase to saturation. The precipitate thus formed is filtered, washed with 30 ml of benzene, and dried to give hydrochloric acid addition salt form of 3,3'-diamino diphenylsulfone crystals. Yield 26.7 g (83%). Recrystallization from 10% hydrous isopropanol gives pure compound, as white needle-like crystals. M.P. 262°–264° C.

Elemental Analysis:

| | C | H | N | S | Cl |
|---|---|---|---|---|---|
| Calc. (%) | 44.8 | 4.4 | 8.7 | 10.0 | 22.1 |
| Found (%) | 45.0 | 4.7 | 8.6 | 10.1 | 22.0 |

EXAMPLE 24

In an autoclave, there are charged 34.3 g (0.1 mol) of 3,3'-dinitro-4-chloro diphenylsulfone, 5.6 g (0.1 mol) of calcium oxide, 2 g of 5% palladium/alumina catalyst and 300 ml of 1,2-dichloro ethane. The reaction is carried out for 9 hours by introducing hydrogen into the autoclave, with the mixture being stirred at 30°–35° C., to keep the pressure at 10 Kg/cm²·G. After the completion of the reaction, the reaction mixture is heated up to 70° C. and subjected to a hot filtering so as to remove the catalyst. On cooling the mixture there are obtained light brown crystals of 3,3'-diamino diphenylsulfone. The crystals are filtered, washed with 10 ml of 1,2-dichloro ethane and dried. Yield 17.6 g (71%). M.P. 170.5°–172° C.

EXAMPLE 25

Reaction of 192 g (1.0 mol) of 4-chlorobenzenesulfonic acid with 135 g (1.2 mols) of chlorobenzene is carried out in the presence of 192 g of Nafion-H (available from Du Pont) under stirring while introducing nitrogen gas and heat-refluxing for 20 hours. The resulting water is separated by means of a water-separating apparatus and unreacted chlorobenzene is recycled to the vessel. After cooling to 70° C., the Nafion-H is filtered out and the filtrate is washed with a small amount of chlorobenzene. The filtrate and washed solution are taken together and subjected to steam distillation. Crude dichlorodiphenylsulfone is obtained. 204 g (yield 71%). Analysis of the crude by means of high performance liquid chromatography is as follows:
4,4'-dichlorodiphenylsulfone: 96.3%
2,4'-dichlorodiphenylsulfone: 3.4%
3,4'-dichlorodiphenylsulfone: 0.14%

The crude is subjected to nitration with a mixed acid of 350 g (3.5 mols) of concentrated $H_2SO_4$ and 360 g (4 mols) of 70% $HNO_3$ at 70°–80° C. for three hours. After cooling the reaction product is poured to ice water, filtered, washed with water and dried. 253 g of light brown granular crude dinitrodichlorodiphenylsulfone are obtained (Total yield 67%).

Then, in a closed glass vessel with a thermometer and stirrer, there are charged 37.7 g (0.1 mol) of the above crude dinitrodichlorodiphenylsulfone, 1 g of 5% Pd/C and 200 ml of ethanol. Hydrogen is introduced while stirring the mixture at 60°–70° C. and 13.7 1 (0.61 mols) of hydrogen are absorbed over 8 hours. Next, 40 g (0.3 mols) of 30% aqueous sodium hydroxide solution are added and hydrogen is further introduced at the same temperature. 4.7 1 (0.21 mols) of hydrogen are absorbed over 3 hours. After completion of the reaction, filtering is effected to remove the catalyst and the filtrate is concentrated to dryness. Light brown crystals thus obtained are washed with water, filtered and dried. 24.3 g of crude 3,3'-diaminodiphenylsulfone are obtained (yield 98%). By high performance liquid chromatography the purity is 98.2%. Recrystallization from ethanol gives slightly brown prism pure crystals. M.P. 172°–174° C.

Elemental Analysis:

| | C | H | N | S |
|---|---|---|---|---|
| Calc. (%) | 58.0 | 4.9 | 11.3 | 12.9 |
| Found (%) | 58.1 | 5.1 | 11.1 | 12.7 |

EXAMPLE 26

211.1 g (0.1 mol) of 4-chlorobenzenesulfonyl chloride is reacted with 135 g (1.2 mols) of chlorobenzene in the presence of 3.2 g of ferric chloride while introducing nitrogen gas. The reaction is carried out under reflux while stirring for 12 hours. After reaction an excess of chlorobenzene is distilled off under reduced pressure at the same temperature.

Analysis of the reaction product by high performance liquid chromatography is as follows:

4,4'-dichlorodiphenylsulfone: 90.4%
2,4'-dichlorodiphenylsulfone: 6.12%
3,4'-dichlorodiphenylsulfone: 1.65%
The remainder: 1.8%

To the above product are added 500 ml of 1,2-dichloroethane and then a mixed acid of 147 g (2.2 mols) of 94% fuming nitric acid and 500 g (5.0 mols) of concentrated sulfuric acid. Reaction is carried out under stirring at 70°–75° C. for 10 hours. After completion of the reaction 500 ml of water are added thereto and the mixed acid phase is separated. Steam is introduced to remove the solvent and brown granules are obtained. After filtering, washing and drying, 351 g of crude dinitrodichlorodiphenylsulfone are obtained (total yield 93.1%).

Then, in a closed glass vessel with a thermometer and a stirrer, there are charged 37.7 g (0.1 mol) of said crude dinitro-dichloro diphenylsulfone, 0.3 g of palladium black and 100 ml of dioxane. While stirring the mixture, at 40°–50° C., there is introduced hydrogen so that 13.9 l (0.62 moles) of hydrogen is absorbed in the mixture during 15 hours. Then, the mixture is added with 24.3 g (0.4 moles) of 28% ammonia water. There is introduced hydrogen, with the mixture being stirred at 40°–50° C., so that 4.42 l (0.196 moles) of hydrogen is absorbed during five hours. After completion of reaction, the mixture is heated up to 70° C. for hot filtering to remove the catalyst. The filtrate is allowed to cool to give slightly brown prism crystals of 3,3'-diamino diphenylsulfone. The crystals are filtered, washed with an aqueous 50% dioxane solution and dried. Yield 20.9 g (84.3%).

EXAMPLE 27

The reduction is carried out in the same manner as in Example 26 except using 37.7 g of the crude dinitrodichlorodiphenylsulfone obtained in Example 26, 5 g of Raney nickel catalyst, 150 ml of ethylcellosolve and 30 g of triethylamine as the dehydrochlorination agent. 17.9 g of 3,3'-diaminodiphenylsulfone are obtained (yield 72%).

What is claimed is:

1. A process for the preparation of 3,3'-diamino diphenylsulfones which comprises catalytically reducing and dehalogenating a diphenylsulfone compound of formula I

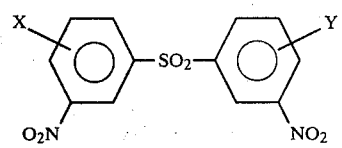

wherein X is a halogen atom and Y is hydrogen or a halogen atom in the presence of a reducing catalyst and a dehydrohalogenating agent.

2. The process of claim 1 wherein the diphenylsulfone compound of formula I is a compound represented by formula II,

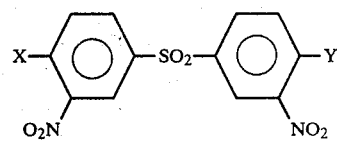

wherein X and Y are the same or different halogen atom.

3. The process of claim 1 wherein the diphenylsulfone compound of formula I is a compound represented by formula III

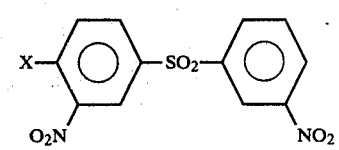

wherein X is a halogen atom.

4. The process of claim 1 wherein the diphenylsulfone compound of formula I is a compound represented by formula IV

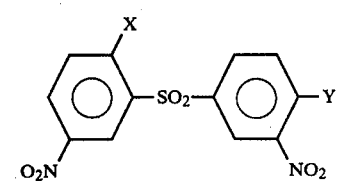

wherein X and Y are the same or different halogen atom.

5. The process of claim 1 wherein the diphenylsulfone compound of formula I is a mixture of dinitrodichlorodiphenylsulfones obtained by nitration of a reaction product mixture obtained by reaction of 4-chlorobenzenesulfonic acid or 4-chlorobenzenesulfonyl chloride with chlorobenzene.

6. The process of claim 2 wherein the diphenylsulfone compound of formula II is 3,3'-dinitro-4,4'-dichlorodiphenylsulfone obtained by nitration of 4,4'-dichlorodiphenylsulfone in an aliphatic halogenated hydrocarbon solvent.

* * * * *

UNITED STATES PATENT AND TRADEMARK OFFICE
CERTIFICATE OF CORRECTION

PATENT NO. : 4,482,742
DATED : November 13, 1984
INVENTOR(S) : Keizaburo Yamaguchi et al It is certified that error appears in the above-identified patent and that said Letters Patent is hereby corrected as shown below:

at Col. 5, line 23; "90-97% of" should read -- 90-97% by -- at Col. 6, line 53; "product" should read -- production -- at Col. 9, Table 1, 6th Column of Table; "React temp. hr"

should read -- React time hr -- at Col. 14, Table III-continued, Example 20, Col. Time (hr),

"9" should read -- 8 --

Signed and Sealed this

Ninth Day of April 1985

[SEAL]

Attest:

DONALD J. QUIGG

Attesting Officer     Acting Commissioner of Patents and Trademarks